United States Patent [19]
Tomisaka et al.

[11] Patent Number: 5,540,661
[45] Date of Patent: Jul. 30, 1996

[54] NEEDLELESS VALVE HAVING A COVALENTLY BONDED LUBRICIOUS COATING

[75] Inventors: Dennis M. Tomisaka, Dublin; Vincent D. McGinniss, Sunbury; David C. Masterson, Grove City, all of Ohio

[73] Assignee: Medex, Inc., Hilliard, Ohio

[21] Appl. No.: 237,197

[22] Filed: May 3, 1994

[51] Int. Cl.[6] .................................................. A61M 25/00
[52] U.S. Cl. ............................ 604/265; 604/256; 604/283; 251/149.1
[58] Field of Search ..................... 604/86–88, 167, 604/169, 230, 244, 246, 256, 265, 283, 905; 251/149, 149.1; 215/247, 249, DIG. 3

[56] References Cited

U.S. PATENT DOCUMENTS

| | | | |
|---|---|---|---|
| 4,568,081 | 2/1986 | Martin | 273/65 |
| 4,856,533 | 8/1989 | Anraku et al. | 128/763 |
| 4,950,257 | 8/1990 | Hibbs et al. | 604/265 |
| 5,061,738 | 10/1991 | Solomon et al. | 523/100 |
| 5,104,389 | 4/1992 | Deem et al. | 604/264 |
| 5,179,174 | 1/1993 | Elton | 525/409 |
| 5,203,775 | 4/1993 | Frank et al. | 604/256 |
| 5,207,656 | 5/1993 | Krarys | 604/256 |

*Primary Examiner*—Corrine M. McDermott
*Attorney, Agent, or Firm*—Wood, Herron & Evans P.L.L.

[57] ABSTRACT

A needleless valve (16), which may be housed in a plastic housing (12), has a web (18) provided with a slit (20) for blunt cannula access therethrough. The web (18) is provided with a lubricious coating (22) on at least a portion thereof, the coating (22) being polymeric and covalently bonded to the web (18). Coating (22) enhances the ease of use of valve (16) and increases its useful life by decreasing the deleterious effects of repeated cannula insertion and removal.

19 Claims, 1 Drawing Sheet

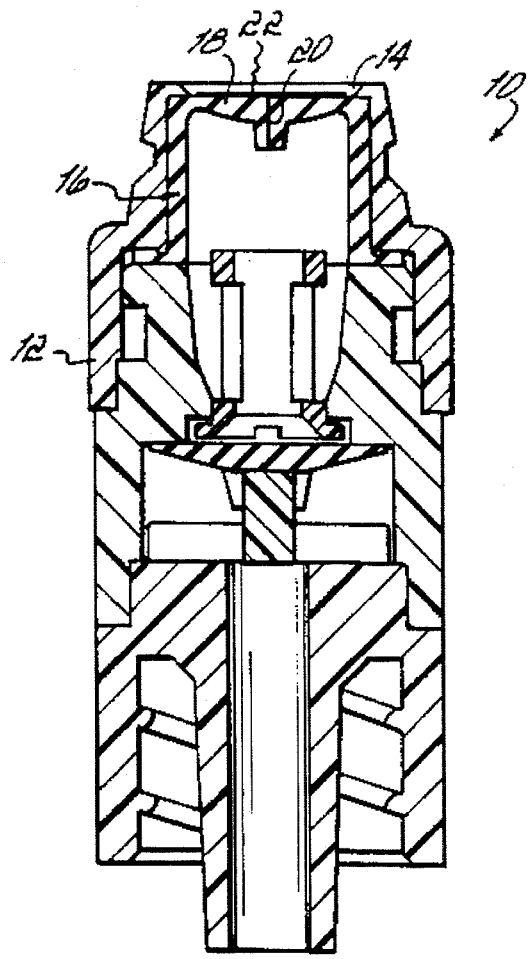
FIG. 1
FIG. 2
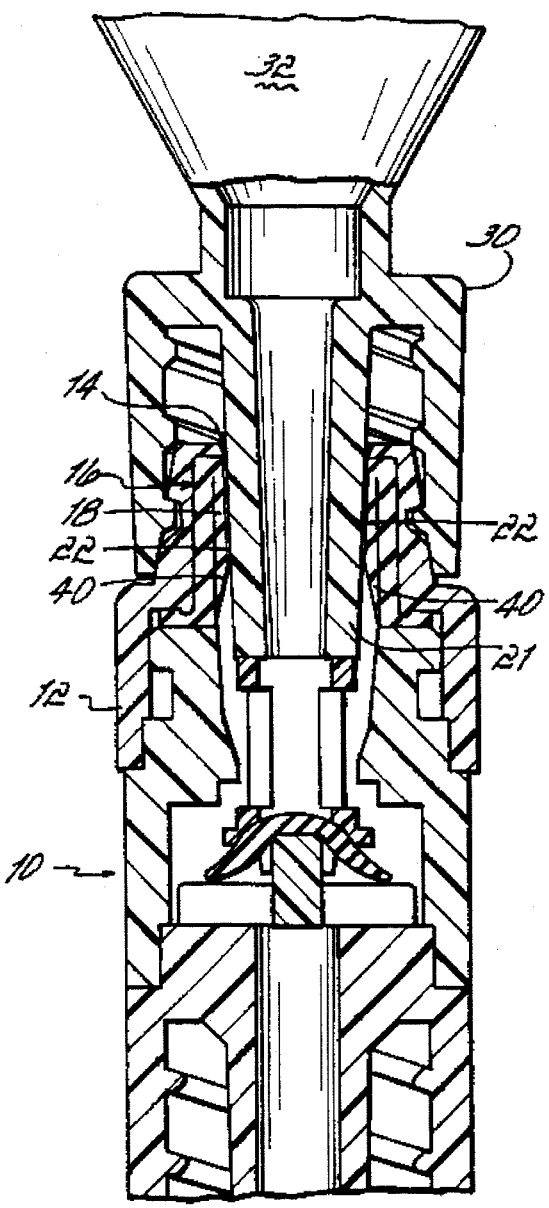
FIG. 3
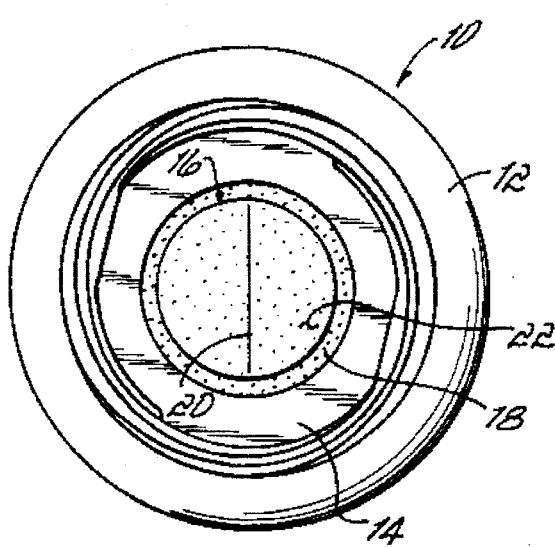

NEEDLELESS VALVE HAVING A COVALENTLY BONDED LUBRICIOUS COATING

FIELD OF THE INVENTION

The present invention relates to needleless medical valves through which fluid may be injected into or withdrawn from a patient, and more specifically, to such valves having improved lubricity to enhance their ease of use and increase their useful life.

BACKGROUND OF THE INVENTION

In many medical situations, it is typical to provide a valve, such as a solid rubber septum on a Y-site or a sample site, which is accessible by a needle piercing through the septum in order to introduce fluids into, or remove blood from, a line coupled to a patient's circulatory system via a catheter inserted into the patient such as through the arm. With such needle-piercable valves, the top of the valve is usually adjacent to or at the top of the valve or site housing and so may be readily wiped clean before each use. While this is advantageous for aseptic purposes, the use of sharp needles presents hazards to medical and other personnel due to the risk of needle sticks which could transmit disease.

In order to reduce or eliminate needle stick problems, it has been proposed to replace the needle-piercable rubber septum with a blunt cannula-accessible valve, such as a rubber piece with a slit septum. The slit septum opens under pressure of a blunt cannula thereagainst to allow the blunt cannula to pass into and through the slit and into communication with the fluid line. This type of needleless valve is shown and described, for example, in U.S. patent application Ser. No. 08/216,640, filed Mar. 23, 1994, assigned to the assignee hereof. The disclosure of the aforesaid application Ser. No. 08/216,640 is incorporated herein by reference.

As will be appreciated, however, repeated insertion and removal of a blunt cannula through a valve having a rubber slit septum may be difficult and may have deleterious effects on the rubber septum, such as tearing thereof, etc., which decreases the useful life of the valve. Thus there has developed a need for an improved needleless valve wherein the use thereof is enhanced and the useful life is extended.

SUMMARY OF THE INVENTION

In its broadest aspects, the present invention provides a rubber valve for a medical device which valve has a valve surface and a slit access through the valve surface. A lubricious coating is covalently bonded to at least a part of the valve surface to enhance the ease of insertion and removal of a blunt cannula access to the valve. The coating is bonded to the valve surface adjacent the slit, and may extend at least partially within the slit. Furthermore, due to the significant elongation/deformation to which the valve surface is subjected during use, the coating preferably is highly extensible. Suitable compositions for the coating material are set forth in detail hereinafter, but generally speaking the coating is a polymeric composition, which may contain silicone and may further contain a wax emulsion. The coating composition may be applied to the web by a suitable spray, dip or brush operation, and is preferably cured thermally or by UV radiation to covalently bond to the valve surface.

In a further aspect of the present invention there is provided a method of adding lubricity to the valve surface of a rubber valve piece having a slit access to be blunt cannula-accessible. In a method of the invention, a lubricious coating of a polymeric material is covalently bonded to at least a portion of the valve surface. The coating, which desirably includes silicone and may further include a wax emulsion, is bonded to the valve surface adjacent the slit and may extend at least partially within the slit. The rubber valve surface may be advantageously pretreated with a chlorine solution prior to bonding the coating thereto to enhance the bonding.

By virtue of the foregoing, there is provided a needleless valve having improved lubricity which enhances its use and its useful life by facilitating access therethrough by a blunt cannula and decreases the potentially destructive effects of repeated blunt cannula access.

These and other objects and advantages of the present invention shall be made apparent from the accompanying drawings and description thereof.

BRIEF DESCRIPTION OF THE DRAWINGS

The accompanying drawings, which are incorporated in and constitute a part of this specification, illustrate an embodiment of the invention and, together with a general description of the invention given above, and the detailed description given below, serve to explain the principles of the invention.

FIG. 1 is a cross-sectional view of a medical site including a needleless valve having a slit valve surface and a lubricious coating in accordance with the principles of the present invention;

FIG. 2 is a top view of the site of FIG. 1; and

FIG. 3 is a cross-sectional view of the site of FIG. 1 with a male luer lock attached thereto for purposes of explaining the principles of the present invention.

DETAILED DESCRIPTION OF THE DRAWINGS

With reference to FIG. 1, there is shown in cross-section an embodiment of a medical device 10 incorporating the features of the present invention. Device 10 in the embodiment shown includes a plastic housing 12 having an access port 14. Housing 12 may be any suitable plastic material (e.g., polycarbonate, Dow Isoplast, rigid PVC, or Ektar). An elastomeric (e.g., silicone or polyisoprene rubber) valve 16 having a valve surface defined by web 18 is associated with housing 12. The web portion 18 of rubber valve 16 is positioned to block access into housing 12 through port 14. A slit 20 is provided through web 18 so that a blunt cannula 21 (see FIG. 3) introduced into port 14 passes through web 18 and into housing 12. To facilitate cannula insertion and removal, a lubricious coating 22 is covalently bonded to web 18, in accordance with principles of the present invention. The coating 22 is desirably a polymeric material.

Web 18 and coating 22 advantageously possess the following properties: (1) both web 18 and coating 22 should be highly extensible in a direction perpendicular to the plane of the web 18; (2) both web 18 and coating 22 should be capable of withstanding the twisting and rotational forces of a blunt cannula 21 during repeated insertion and removal operations through the web 18; (3) both web 18 and coating 22 should be resistant to breakdown or chemical attack by cleaning solutions, including disinfectants such as alcohol, betadine, etc.; and (4) the coated web 18 should be resistant to abrading and other wear and tear during cannula 21 insertion and removal and cleaning operations.

FIG. 2 is a top view of the medical device 10 shown in FIG. 1 wherein coating 22 is shown bonded to web 18 adjacent or surrounding the slit 20. While web 18 is shown partially but not completely coated with coating 22, it is contemplated that web 18 may be completely coated and that the entire valve 16 may be coated. It will be appreciated that coating 22 may extend at least partially within slit 20 or perhaps completely along slit 20. As shown in FIG. 3, a blunt cannula 21 of a luer lock 30 is inserted into and through slit 20 of web 18. As is well known, luer lock 30 could be part of a syringe 32. As cannula 21 of luer lock 30 is inserted through slit 20, the portions of web 18 to either side of slit 20 flex downwardly and outwardly to either side of the blunt cannula 21 like lips, as at 40 in FIG. 3. The coating 22 on web 18 enhances the ease of insertion and removal of cannula 21 of luer lock 30 and reduces the destructive, tearing effects which may otherwise occur. In this way, coating 22 enhances the useful life of the rubber valve 16 in medical device 10, as it can be accessed repeatedly without damage thereto.

Various coating materials 22 will now be described in detail with reference to the following examples. In each of the following examples, the coating materials were applied to a polyisoprene rubber valve 16. It will be appreciated, however, that other elastomeric materials, such as silicone could be used for the valve 16.

EXAMPLES

In Table 1 below, there are tabulated various coating formulations which have been tested.

TABLE 1

| Coating Number | Coating Formulation |
| --- | --- |
| 1 | 10 gms DEHESIVE[1] Silicone 410E<br>1.5 gms CROSSLINKER V20[2] |
| 2 | 10 gms DEHESIVE Silicone 920<br>0.25 gms CROSSLINKER V24[2]<br>0.2 gm catalyst OL[2] |
| 3 | 10 gms DEHESIVE Silicone 920<br>0.25 gms CROSSLINKER V24<br>0.1 gm catalyst OL<br>2.6 gms toluene |
| 4 | 10 gms DEHESIVE Silicone 410L<br>1.5 gms CROSSLINKER V20 |
| 5 | 5 gms of coating #1<br>0.16 gms Dow Corning 175[3] |
| 6 | 3 gms of coating #1<br>0.1 gm Michelman Wax Emulsion 30560[4] |
| 7 | 26.1 gms DEHESIVE 410E<br>3.9 gms CROSSLINKER V20<br>1 gm Michelman Wax Emulsion |

TABLE 1-continued

| Coating Number | Coating Formulation |
| --- | --- |
| 8 | 30560<br>26.1 gms DEHESIVE 410E<br>3.9 gms CROSSLINKER V20 |
| 9 | 5 gms of coating #8<br>0.6 gms Neo Rez R-967[5] |
| 10 | 5 gms of coating #8<br>0.7 gm Neo Rez R-972[5] |
| 11 | 5 gms of coating #8<br>0.8 gm Witcobond W234[6] |

[1]DEHESIVE silicones are available from Wacker Silicones Corp., Adrian, MI.
[2]CROSSLINKER V20 and V24 and catalyst OL are available from Wacker Silicones Corp., Adrian, MI.
[3]Dow Corning 175 is a nonionic, high molecular weight polymethylsiloxane emulsion that is a mar/slip resistance additive.
[4]Michelman Wax Emulsion 30560 is an experimental, nonionic wax emulsion available from Michelman, Inc., Cincinnati, OH.
[5]Neo Rez R-967 and R-972 are aliphatic urethane dispersions available from ICI.
[6]Witcobond W234 is an aliphatic urethane dispersion (30% solids) available from Witco Corp., Organic Div., New York.
[6], Witcobond W234 is an aliphatic urethane dispersion (30% solids) available from Witco Corp., Organic Div., New York.

The above-identified coating formulations are relatively low molecular weight polymer-containing formulations which, upon curing, form cross-linked, higher molecular weight polymeric coatings. In the examples tabulated in Table 2 below, the specifically referenced coating formulation was applied to the noted valve type using conventional spray gun techniques and thereafter thermally cured for 15 minutes at 70° C. to covalently bond the coating to the valve surface. Where indicated, a chlorination pretreatment step was utilized that consisted of soaking the valve surface (either by soaking the entire valve body or just the tip end containing the valve surface, as designated) in a 0.3% chlorine solution for the noted period of time, followed by a water rinse, immersion for 30 seconds in a 2% solution of ammonium hydroxide, a final water rinse, and oven drying for 5 minutes at 70° C. The chlorine surface treatment was intended to clean the valves and enhance adhesion of the coating system.

In the testing protocol and unless otherwise noted, the cannula 21 of a standard male luer lock (MLL) 30 was inserted and removed repeatedly from the coated valve to simulate actual use conditions. Additionally, the coated web surface was wiped with isopropyl alcohol between each reuse to simulate a typical cleaning operation in practice, unless otherwise noted.

Finally, while no specific thickness data is given, it is contemplated that coating thickness in the range of 0.1–75 microns will be suitable.

TABLE 2

| Sample No. | Valve Type | Chlorination (time) overall | Chlorination (time) tip | Coating No. | Number of Luer Lock Reuses | Comments |
| --- | --- | --- | --- | --- | --- | --- |
| 1 | A | 5 mins. | — | #2 | 31/47 | |
| 2 | B | — | — | #3 | 13/19 | |
| 3 | A (textured) | 5 mins. | — | #2 | 56 | Tested with no alcohol wiping between uses; no tearing observed; |

TABLE 2-continued

| Sample No. | Valve Type | Chlorination (time) overall | tip | Coating No. | Number of Luer Lock Reuses | Comments |
|---|---|---|---|---|---|---|
| 4 | A (textured) | 5 mins. | — | #2 | 85 | valve was buckled torsionally and very concave No tearing observed; used polypropylene syringe instead of polycarbonate male luer lock for testing |
| 5 | B (smooth) | 5 mins. | — | #2 | 44 | Valve was torn at edge of slit |
| 6 | B | — | — | #4 | 73 | Valve was torn at edge of slit |
| 7 | B | 5 mins. | — | #4 | 50 | Possible small radial tear |
| 8 | B | 5 mins. | — | #5 | 45 | No tear visible; valve highly concave |
| 9 | B | 5 mins. | — | #6 | 85 | No tearing of valve was observed |
| 10 | B | — | — | #7 | 59 | |
| 11 | B | 5 mins. | — | #7 | 52 | |
| 12 | B | — | — | #7 | 52 | |
| 13 | B | — | — | #9 | 9 | |
| 14 | B | — | — | #10 | 21 | |
| 15 | B | — | — | #11 | — | |
| 16 | B | 5 mins. | — | #9 | 21 | |
| 17 | B | 5 mins. | — | #10 | 64 | |
| 18 | B | 5 mins. | — | #11 | 27 | |

An additional formulation was developed to test various methods of applying the coating to the valve. The formulation utilized for that testing was as follows:

26.1 gms DEHESIVE 410E 1 gm Michelman Wax Emulsion 30560

3.9 gms CROSSLINKER V20

A series of valves 12 were spray coated (with a Binks spray gun) with the above formulation and using one of the following protocols: (1) valves coated with a 2-pass spray application, followed by curing for 15 minutes to 70° C. to covalently bond to the valve surface; (2) valves coated with a 4-pass spray application, followed by curing for 15 minutes at 70° C. to covalently bond to the valve surface; and (3) valves coated with a 2-pass spray application, coating cured for 15 minutes at 70° C. to covalently bond to the valve surface, followed by an additional 2-pass spray application, and subsequent curing at 70° C. for 15 minutes. Each of the above methodologies is believed to provide reproducible coating weights. It is contemplated that ultrasonic spray coating, such as is available from Sono-Tek Corp., Poughkeepsie, N.Y. could be utilized.

In the present invention, a valve 16 having a valve surface, such as a web 18, is housed in a housing 12. Web 18 has a polymeric, lubricious coating 22 covalently bonded thereto. During use, a blunt cannula 21 is repeatedly inserted through and removed from slit 20 and coating 22 enhances the ease of doing so and increases the useful life of the valve 16 by reducing the destructive effects of such repeated use.

While the present invention has been illustrated by the description of an embodiment thereof and specific examples, and while the embodiment has been described in considerable detail, it is not intended to restrict or in any way limit the scope of the appended claims to such detail. Additional advantages and modifications will readily appear to those skilled in the art. For example, it is contemplated that a linkage element or compound could be attached to the rubber valve surface and that a desired lubricious coating formulation would then be covalently bonded to the linkage element. Also, the valve surface may be the surface of a thick valve member (other than a web). Additionally, it is contemplated that the rubber valve can be temporarily swelled by immersion in a solvent (e.g., toluene) system containing a silicone oil or uncured silicone polymer. It is believed this would allow the silicone to ingress into the rubber matrix, leaving a lubricated surface once the solvent was driven off. The invention in its broader aspects is therefore not limited to the specific details, representative apparatus and methods and illustrative examples shown and described. Accordingly, departures may be made from such details without departing from the scope or spirit of applicants' general inventive concept.

Having described the invention, what is claimed is:

1. In a medical device having a housing with an access port including a rubber valve associated with the housing, the rubber valve having a valve surface positioned to block access into the housing through the port and a slit through the valve surface so that a blunt cannula introduced into the port passes through the valve surface and into the housing, the improvement comprising:

a lubricious polymeric coating not requiring hydration for its lubricity covalently bonded to at least a portion of the valve surface.

2. In the medical device of claim 1 wherein the coating is bonded to the valve surface adjacent the slit.

3. In the medical device of claim 2 wherein the coating extends at least partially within the slit.

4. In the medical device of claim 1 wherein the coating extends at least partially within the slit.

5. In the medical device of claim 1 wherein the coating is highly extensible.

6. In the medical device of claim 1 wherein the coating contains silicone.

7. In the medical device of claim 6 wherein the coating further contains a wax emulsion.

8. In the medical device of claim 1 wherein the valve surface is defined by a web.

9. In the medical device of claim 1 wherein the valve surface has been pretreated with a chlorine solution prior to said lubricious polymeric coating being covalently bonded to at least a portion of the valve surface.

10. In a rubber valve having a valve surface and a slit access through the valve surface, the improvement comprising:
a lubricious coating not requiring hydration for its lubricity covalently bonded to at least a portion of the valve surface.

11. In the rubber valve of claim 10 wherein the coating is bonded to the valve surface adjacent the slit.

12. In the rubber valve of claim 11 wherein the coating extends at least partially within the slit.

13. In the rubber valve of claim 10 wherein the coating extends at least partially within the slit.

14. In the rubber valve of claim 10 wherein the coating is highly extensible.

15. In the rubber valve of claim 10 wherein the coating is polymeric.

16. In the rubber valve of claim 15 wherein the coating contains silicone.

17. In the rubber valve of claim 16 wherein the coating further contains a wax emulsion.

18. In the rubber valve of claim 10 wherein the valve surface is defined by a web.

19. In the rubber valve of claim 10 wherein the valve surface has been pretreated with a chlorine solution prior to said lubricious coating being covalently bonded to at least a portion of the valve surface.

* * * * *